(12) United States Patent
Graf et al.

(10) Patent No.: US 8,643,361 B2
(45) Date of Patent: Feb. 4, 2014

(54) NEEDLE HEAD

(75) Inventors: Markus Graf, Zürich (CH); Hans Eggenberger, Rüti (CH); Martin Fitzi, Stäfa (CH); Christoph Schanz, Stäfa (CH)

(73) Assignee: Sensirion AG, Stafa (CH)

( * ) Notice: Subject to any disclaimer, the term of this patent is extended or adjusted under 35 U.S.C. 154(b) by 440 days.

(21) Appl. No.: 13/068,743

(22) Filed: May 19, 2011

(65) Prior Publication Data
US 2012/0013326 A1 Jan. 19, 2012

(30) Foreign Application Priority Data
Jul. 14, 2010 (EP) .................................. 10007235

(51) Int. Cl.
*G01R 1/06* (2006.01)
(52) U.S. Cl.
USPC . 324/149; 324/514; 324/762.05; 324/762.02; 324/758.03; 324/757.03; 324/754.01; 324/756.04; 324/755.11; 324/756.01
(58) Field of Classification Search
USPC .......... 324/149, 514, 762.05, 762.02, 758.03, 324/757.03, 754.01, 756.04, 755.11, 756.01
See application file for complete search history.

(56) References Cited

U.S. PATENT DOCUMENTS

| | | | |
|---|---|---|---|
| 3,832,882 A | 9/1974 | Schoen, Jr. | |
| 4,120,206 A * | 10/1978 | Rud, Jr. | 73/718 |
| 4,177,667 A | 12/1979 | Rolf et al. | |
| 4,399,707 A * | 8/1983 | Wamstad | 73/727 |
| 4,590,789 A | 5/1986 | Kunze | |
| 4,658,651 A * | 4/1987 | Le | 73/708 |
| 4,730,496 A * | 3/1988 | Knecht et al. | 73/724 |
| 4,733,533 A | 3/1988 | Deininger et al. | |
| 4,777,716 A | 10/1988 | Folk et al. | |
| 4,798,089 A * | 1/1989 | Frick et al. | 73/706 |
| 4,825,684 A | 5/1989 | Nishiguchi et al. | |
| 4,841,777 A * | 6/1989 | Hershey et al. | 73/721 |
| 4,944,187 A * | 7/1990 | Frick et al. | 73/718 |
| 4,972,716 A * | 11/1990 | Tobita et al. | 73/721 |
| 5,133,215 A * | 7/1992 | Lane et al. | 73/756 |
| 5,267,467 A | 12/1993 | Caron | |
| 5,285,690 A * | 2/1994 | Koen et al. | 73/727 |
| 5,407,501 A * | 4/1995 | Koen et al. | 156/64 |
| 5,410,259 A * | 4/1995 | Fujihara et al. | 324/750.23 |
| 5,604,444 A | 2/1997 | Harwood et al. | |
| 5,659,125 A | 8/1997 | Ernst | |

(Continued)

FOREIGN PATENT DOCUMENTS

| | | |
|---|---|---|
| EP | 2259027 | 12/2010 |
| JP | 58095167 | * 5/1983 |

(Continued)

*Primary Examiner* — Patrick Assouad
*Assistant Examiner* — Lamarr Brown
(74) *Attorney, Agent, or Firm* — Cooper & Dunham LLP

(57) ABSTRACT

The present idea refers to a needle head, its use in a probe arrangement, and a method for electrically contacting multiple electronic components. The needle head comprises a body with a lower surface, needle electrodes emerging from the lower surface, and multiple outlets arranged in the lower surface. A channel is arranged between an inlet in the body and the outlets for conveying a medium from the inlet to the outlets. By this means, electronic components arranged in close distance under the lower surface of the needle head are directly exposed to the medium which provides a test environment during a test of the electronic components.

20 Claims, 4 Drawing Sheets

(56) References Cited

U.S. PATENT DOCUMENTS

| | | | |
|---|---|---|---|
| 5,804,983 A | 9/1998 | Nakajima et al. | |
| 5,807,104 A * | 9/1998 | Ikeya et al. | 439/73 |
| 5,848,122 A | 12/1998 | Kurtz | |
| 5,906,718 A * | 5/1999 | Hance et al. | 204/412 |
| 5,907,246 A * | 5/1999 | Abraham et al. | 324/750.08 |
| 5,963,027 A | 10/1999 | Peters | |
| 6,094,056 A * | 7/2000 | Bardsley et al. | 324/756.01 |
| 6,130,543 A * | 10/2000 | Iino | 324/750.2 |
| 6,134,941 A | 10/2000 | Cripe et al. | |
| 6,208,155 B1 * | 3/2001 | Barabi et al. | 324/750.25 |
| 6,239,590 B1 * | 5/2001 | Krivy et al. | 324/750.02 |
| 6,286,363 B1 | 9/2001 | Discenzo | |
| 6,359,253 B1 | 3/2002 | Sritulanont et al. | |
| 6,418,783 B2 | 7/2002 | Sunshine et al. | |
| 6,498,505 B2 * | 12/2002 | Liao et al. | 324/756.01 |
| 6,688,156 B2 | 2/2004 | Dietrich et al. | |
| 6,690,569 B1 | 2/2004 | Mayer et al. | |
| 6,750,522 B1 | 6/2004 | Mayer et al. | |
| 6,769,285 B2 | 8/2004 | Schneider et al. | |
| 7,281,405 B2 | 10/2007 | Mayer et al. | |
| 7,758,675 B2 * | 7/2010 | Naito et al. | 96/61 |
| 7,900,496 B2 | 3/2011 | Mayer et al. | |
| 8,033,180 B2 * | 10/2011 | Morales et al. | 73/760 |
| 2003/0136677 A1 * | 7/2003 | Neumann et al. | 204/426 |
| 2004/0108847 A1 | 6/2004 | Stoll et al. | |
| 2004/0201389 A1 * | 10/2004 | Jun | 324/754 |
| 2004/0256959 A1 | 12/2004 | Ladabaum | |
| 2005/0237070 A1 * | 10/2005 | Kazama | 324/754 |
| 2005/0241175 A1 | 11/2005 | Howland, Jr. et al. | |
| 2006/0145711 A1 | 7/2006 | Honma | |
| 2007/0024312 A1 | 2/2007 | Rittberger et al. | |
| 2007/0045128 A1 * | 3/2007 | Krafthefer et al. | 205/778.5 |
| 2009/0093161 A1 * | 4/2009 | Kazama et al. | 439/620.01 |

FOREIGN PATENT DOCUMENTS

| | | |
|---|---|---|
| JP | 10160597 | 6/1998 |
| JP | 2001281267 | 10/2001 |
| WO | 9904276 | 1/1999 |
| WO | WO0140784 | 6/2001 |
| WO | WO0142776 | 6/2001 |
| WO | 02101348 | 12/2002 |

* cited by examiner

NEEDLE HEAD

CROSS REFERENCE TO RELATED APPLICATIONS

This application claims the priority of European Patent Application 10007235.4, filed Jul. 14, 2010, the disclosure of which is incorporated herein by reference in its entirety.

BACKGROUND OF THE INVENTION

Sensors according to the state of the art often are provided as integrated sensors on semiconductor chips.

Such sensors may be humidity sensors which use a layer of a humidity sensitive material arranged on a semiconductor chip, as it is described in WO 01/42776. Other types of sensors e.g. use metal oxide technologies and are adapted to measure various types of substances in gases or liquids. Typical substances that can be measured are e.g. $CO$, $CO_2$, $NO_x$, volatile organic compounds (VOC), in particular any type of gaseous organic compounds, and any other types of compound.

Semiconductor chips are usually manufactured in wafers, where each wafer may comprise hundreds or more chips. After manufacturing, the wafers are cut to separate the chips from each other, place them in a suitable housing and calibrate each sensor individually by exposure to fluids of known composition, as it is e.g. described in WO 01/40784.

For improving the calibration process it is suggested to calibrate the sensors prior to separating the semiconductor chips which also is called as calibration on a "wafer level". For implementing such calibration routine, U.S. Pat. No. 7,281,405 B1 discloses an apparatus with a chuck for holding a wafer with sensors to be calibrated, and a lid arranged above the chuck and facing the wafer. The lid provides an opening in which a probe head is arranged. The probe head has the form of a flat plate fixed to the lid and an opening at its centre. Needle electrodes in form of cantilevers are fixed at the lower surface of the plate. The chuck may be moved laterally with respect to the lid such that the needle electrodes can be positioned on suitable pads on the wafer for producing calibration measurements. In order to expose the sensors on the wafer to a calibration environment, the lid includes a circular feed duct and small openings facing the wafer for providing calibration gas supplied via the feed duct and emanating from the small openings.

However, since the probe head is located in the middle of the lid and is fixed within the opening of the lid, there cannot be calibration gas supplied directly to this area. On the other hand, this area represents the location where the measurement is performed by means of the needle electrodes, such that it is unfortunate that this location cannot be directly exposed to the calibration gas.

BRIEF SUMMARY OF THE INVENTION

The problem to be solved by the present invention is therefore to provide an apparatus and a method for improving the measurement environment in the close vicinity of an electronic component currently investigated.

This problem is solved according to a first aspect of the present invention by a needle head according to the features of independent claim 1. The needle head is designed for electrically contacting an electronic component and comprises a body with a lower surface and needle electrodes emerging from the lower surface. In addition, there are provided multiple outlets arranged in the lower surface. A channel between an inlet in the body and the outlets is provided for conveying a medium from the inlet to the outlets.

By implementing a medium supply through the needle head and having the medium pour directly onto the one or more electronic components presently under test, the testing environment is improved. Consequently, even more accurate test results may be generated, and—provided the test is implemented as a calibration routine—such improved testing environment will also improve the operation of the electronic component, as more accurate calibration parameters will be generated and used for interpreting a measured signal of the electronic component in operation. The test environment, which may include, for example, a well-defined gas concentration to which the electronic component shall be exposed to, is improved since the electronic component under test is directly loaded with such gas for the reason that the outlet for the gas is arranged in the needle head in the immediate vicinity of the electronic component to be tested. It is noted, that the electronic component may preferably be a sensor, however, it may also be any other electronic component with a need for exposure to a test environment. The reason for exposing such electronic component to a test environment may be testing the component, or, for example, calibrating the component. The medium used for establishing the test environment may be any medium such as a gas or a liquid to which the electronic component is expected to be exposed to in operation.

Such needle head may advantageously be integrated into a probe arrangement with a panel, a channel in such panel, and at least one outlet arranged in a lower surface of the panel, wherein a medium supplied to the channel may emanate from the channel through the outlets of the panel. In such arrangement, the wafer may also be exposed to the medium in its periphery such that a large area is exposed to the test environment which is beneficial for the reliability and accurateness of the measurement. In such embodiment, the channel in the panel may be connected to the channel in the needle head and provide the medium to the needle head via the panel. Alternatively, the medium may be supplied to the needle head by other means outside the panel. In another embodiment of a probe arrangement, the channels in the panel and the needle head are connected such that the medium emanating from the needle head is supplied via the panel. However, it may not be necessary that the medium additionally emanates from the panel itself for exposing also the periphery of the wafer to the medium. Such effect may also be achieved by other medium supply means.

According to another aspect of the present invention, there is provided a method for electrically contacting multiple electronic components, in which a wafer including the electronic components is provided as well as a needle head. The inlet of the needle head is supplied with the medium the electronic components shall be exposed to. Multiple of these electronic components are contacted simultaneously by the needle electrodes. Signals accessible at the needle electrodes are measured, preferably simultaneously for multiple electronic components. These signals are measured when the electronic component is impacted by the medium transferred through the needle head.

By means of this method, a test or calibration routine may be implemented for multiple electronic components simultaneously, thereby substantially saving time in the production process.

For other advantageous embodiments it is referred to the dependent claims. It is noted that embodiments referred to or claimed only in connection with the apparatus shall be disclosed in connection with the method, too, and vice versa.

BRIEF DESCRIPTION OF THE DRAWINGS

A number of embodiments of the present invention will now be described by way of example only and with reference to the accompanying drawings, in which the figures show.

DETAILED DESCRIPTION OF THE DRAWINGS

Figure 1:
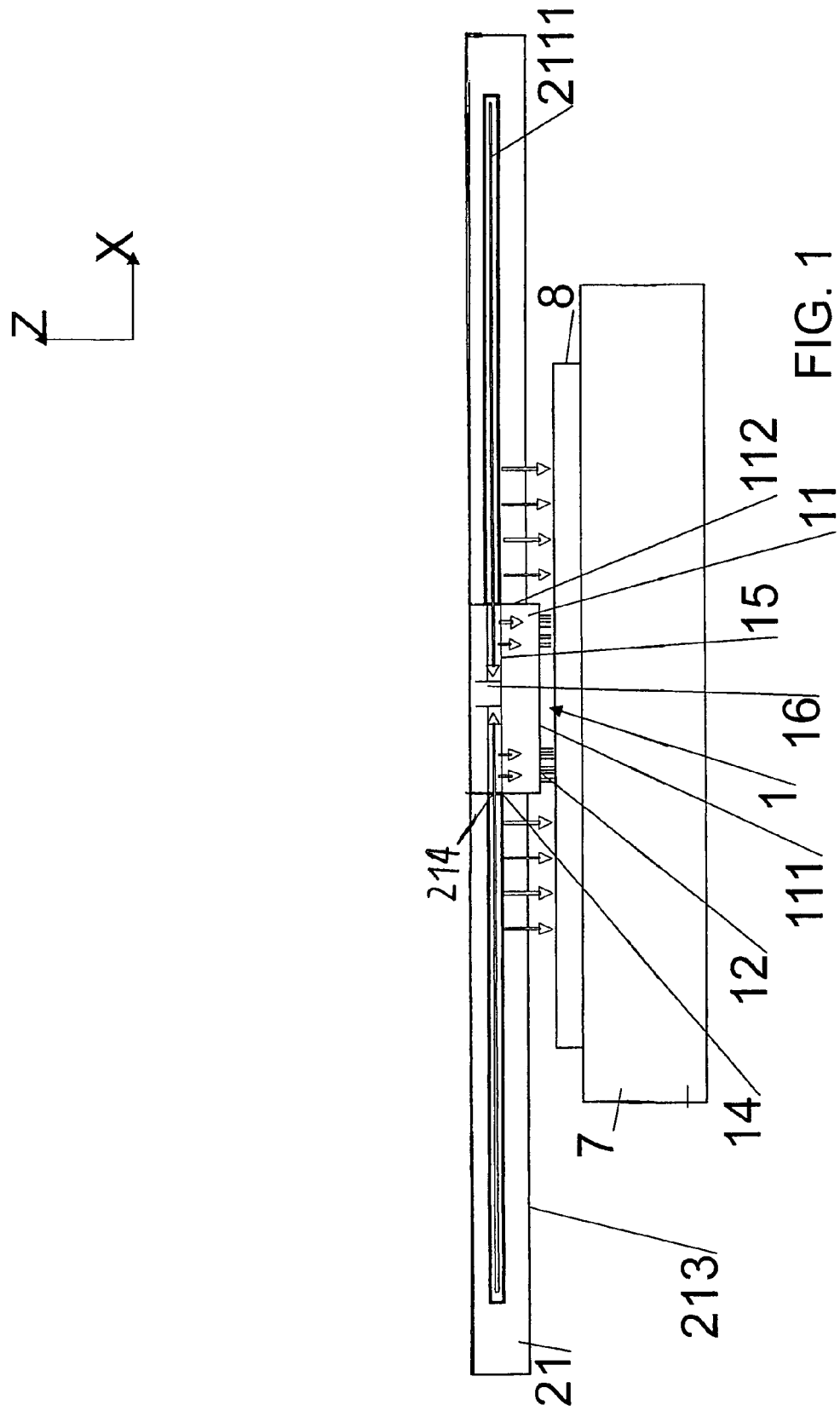
FIG. 1 a schematic illustration of a wafer prober in a sectional view according to an embodiment of the present invention, FIG. 2 a sectional view of a needle head according to an embodiment of the invention, interacting with a circuit board and a panel, FIG. 3 a perspective view of a needle head according to an embodiment of the invention, FIG. 4 a plan view of the lower surface of the needle head of FIG. 3, and FIG. 5 a cut open view of the needle head according to FIG. 3.

In the figures, like or similar elements are referred to by the same reference numerals across all figures.

FIG. 1 shows a sectional view of an apparatus for testing and/or calibrating electronic components, and especially for testing and/or calibrating sensors. In particular, the apparatus may be used for calibrating humidity sensors. Humidity sensors may be used to detect the amount of water in air or in another gas.

For the reason that these sensors are calibrated while still being arranged in a common wafer such apparatus generally is also called a "wafer prober". Accordingly, calibration measurements are carried out while the sensors are still assembled in the wafer by exposing the wafer to a fluid, e.g. in form of a gas, with a known amount of the substance to be measured. Rather than first cutting the wafer, housing the sensors and then calibrating them, the sensors are calibrated at an early stage. This allows calibrating a large number of sensors quickly and eliminating malfunctioning sensors from further manufacturing steps. Furthermore, it requires only a small volume of calibration fluid for calibrating a large number of sensors.

A substantially cylindrical chuck 7 acts as a support for such a wafer 8. Wafer 8 comprises a two-dimensional matrix of sensors that are basically ready for operation but that still need to be calibrated, cut and, where applicable, packaged. Wafer 8 rests on a flat top surface of chuck 7. Chuck 7 can optionally be equipped with suction ducts (not shown) ending in the chucks top surface and being used to hold wafer 8 stationary on chuck 7 as known by the person skilled in the art.

Facing a top side of the chuck 7—respectively the wafer(s) 8 loaded onto chuck 7 during operation—there is arranged a panel 21. Between a bottom surface 213 of the panel 21 and the top surface of the chuck or the wafer 8 there is provided a small gap.

A needle head 1 is arranged in an opening 214 of the panel 21 and may be rigidly connected to the panel 21. Needle electrodes 12 are emerging from a lower surface 111 of a body 11 of the needle head 1. "Emerging" in this context means that the needle electrodes not necessarily protrude every element of the body 11 in the direction facing the wafer 8. Given that, according to embodiments explained later on, the lower surface of the body may be built from an element with a planar surface which the needle electrodes perforate, the needle electrodes do emerge from and relative to such element building the lower surface of the needle head. These needle electrodes are arranged such that their tips can contact pads of the sensor chips on wafer 8.

The panel 21 comprises a channel 2111 for guiding a medium to the wafer 8 in order to expose the sensors on the wafer 8 to a testing or calibration environment. For this reason, gas from a reservoir not shown in this Figure may be fed into channel 2111 via a suitable supply structure not shown in this Figure either. Once entering the channel 2111, the gas may emanate from outlets arranged in the bottom surface 213 of the panel 21. These outlets may be radially arranged in the panel 21 between an opening 214 for the needle head 1 and a virtual peripheral edge in the panel 21 representing the edge of the centred wafer 8 on chuck 7. Although the outlets themselves are not shown in FIG. 1, their position is indicated by means of vertical arrows denoting the gas emanating from the wafer and pouring down towards the wafer 8.

The horizontal channel 2111 in the panel 21 is aligned with a horizontal channel 15 in the needle head 1. For alignment purposes a horizontal outlet in the opening 214 of the panel 21 is aligned with a horizontal inlet 14 of the needle head 1 at its side surface 112 such that the two channels 2111 and 15 are connected. This results in gas being supplied to the channel 2111 not only emanating from the vertical outlets of the panel 21 towards the wafer 8 but also pouring into the channel 15 of the needle head 1. In general, the number of inlets at the needle head is not restricted to one. There may be more inlets arranged and connected to the channel of the needle head as deemed to be appropriate.

The lower surface 111 of the needle head 1 includes multiple outlets—not shown in the present Figure—connected with the channel 15 of the needle head 1. As a consequence, gas supplied to the channel 15 emanates from the lower surface 111 of the needle head 1 and evaporates the wafer 8 as indicated by arrows in FIG. 1. By this means a direct exposure of the sensors located under the needle head 1 to the gas can be achieved during probing/testing/calibrating resulting in more accurate results.

In the specific needle head 1 of FIG. 1, a plug 16 is provided for closing an opening at a top side of the needle head 1 for preventing gas from pouring out of such opening. Alternatively, such opening may be used as inlet for gas supplied from the top of the needle head instead of the gas supplied through the panel 21.

The panel may be mounted to a suitable support structure. There may be means provided for heating and/or cooling the panel and/or the needle head. Such heating/cooling means serve for adjusting a temperature of the medium prior to leaving the panel and/or the needle head. The needle electrodes may be electronically connected to the outside world by suitable leads which are bonded or soldered to the needle head.

While a humidity generator may be used for preparing a gas having a known, well-defined humidity and supplying such gas to the channel 2111, alternatively the whole apparatus of FIG. 1 may be placed into a chamber containing a gas with a known humidity, e.g. in a climate controlled cabinet, where possibly the composition of the gas is not well known in advance.

Chuck 7 and panel 21 may be moved relative to each other in x and y direction. In case of implementing the test device in a stand, the chuck 7 or any other means for carrying the chuck 7 may be movable with respect to the panel 21. Such positioning device is able to accurately position the chuck 7 along the horizontal directions x and y. Direction x is illustrated by an arrow in FIG. 1 while direction y is perpendicular to the image plane. Optionally, panel 21 and chuck 7 may be mutually displaceable along the z-direction for slightly separating the two parts while x-y-positioning device moves the chuck 7. The x-y-positioning device may alternatively comprise a robot arm carrying chuck 7. Robot arm can be used for displacing chuck 7 in respect to needle head 1 and also for bringing chuck 7 to a transfer position remote from needle head 1 for unloading and loading a wafer 8. For contacting the individual sensors with the needle electrodes 12 of needle head 1, the panel 11 or the needle head 1 may again be mounted to a suitable z-positioning device. The positioning device may be controlled by a control unit. The control unit controls the operation of x-, y- and z-actuators of a wafer prober adapted to contact each individual sensor on a wafer by means of a needle head. The control unit may further include circuitry and/or software for operating the sensors contacted by the needle head and for calibrating the same, e.g. by storing calibration data on a memory device integrated with each sensor. Control unit may also control the operation of a humidity generator in case the sensors to be calibrated are humidity sensors, which humidity generator basically is a device that adds and/or removes humidity to/from a volume of gas until the same has a given level of humidity.

The wafer prober according to FIG. 1 may additionally provide means for heating and/or cooling the chuck 7 to a given temperature thereby substantially controlling the temperature of the wafer 8 arranged on top of the chuck 7.

Figure 2:
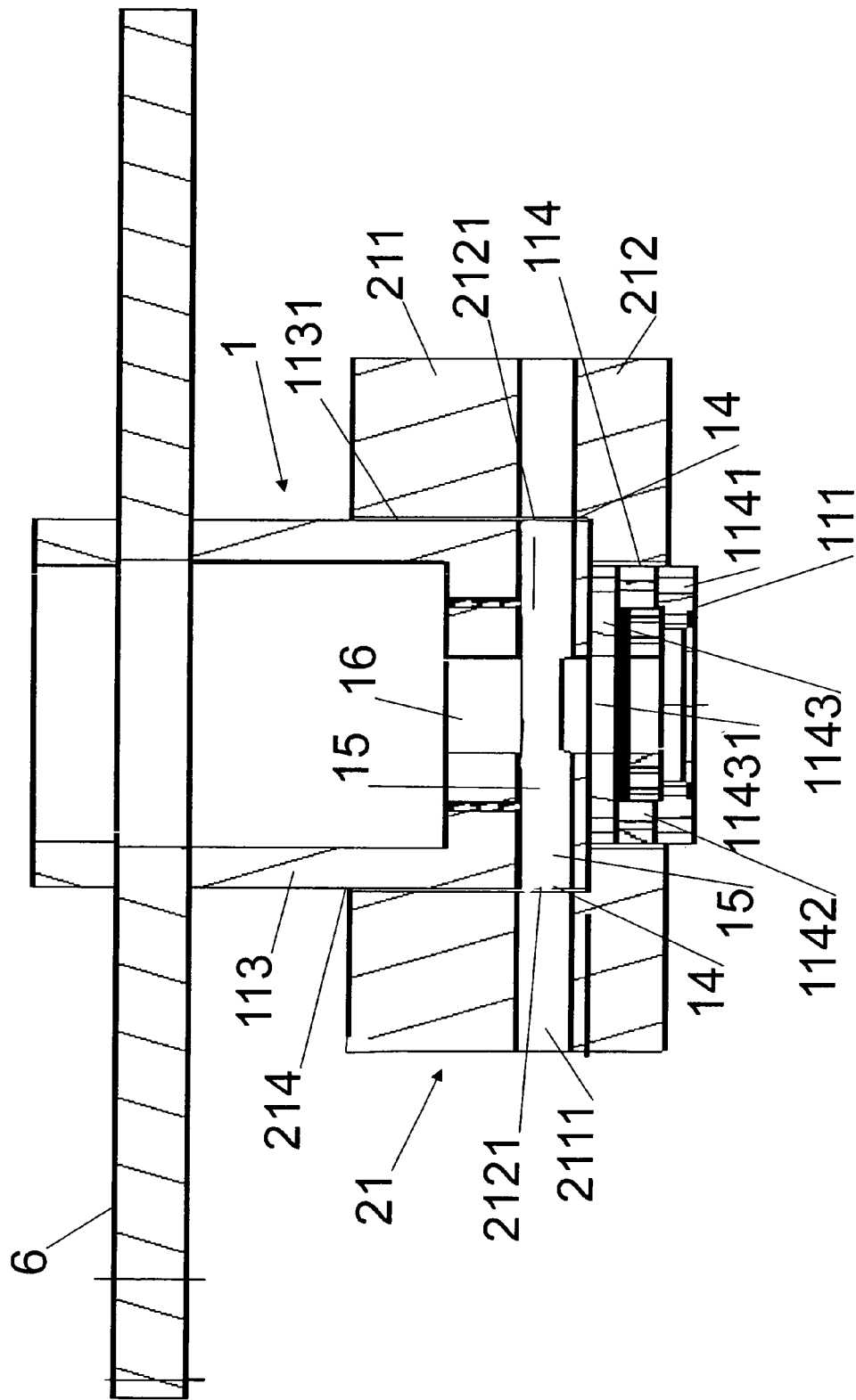

FIG. 2 illustrates a sectional view of a needle head 1 according to another embodiment of the invention. In contrast to the needle head of FIG. 1, the present needle head 1 is directly mounted to a circuit board 6 and electrically connected to it by leads (not shown). Further, the needle head 1 of FIG. 2 includes a frame 113, preferably made of metal and in particular made out of aluminium, and a layered needle holder 114 comprising three ceramic layers: A top layer 1143 holds the needle electrodes (not shown) which preferably are pressed into the ceramic material of the top layer 1143. An intermediate layer 1142 is designed as a frame and may act as a spacer towards a bottom layer 1141 by that defining a chamber 1144 between the top layer 1143 and the plain bottom layer 1141. The bottom layer 1141 comprises bores for the needle electrodes to protrude wherein the needle electrodes typically are not fixed in these bores. Instead, the needle electrodes may reach through the bores and slightly emerge from the lower surface 111 of the bottom layer 1141. They may show a certain degree of flexibility in z-direction needed for contacting pads on the wafer 8 whereas the bores may prevent from an excessive lateral movement of the needle electrodes.

Additionally, the bottom layer 1141 comprises outlets for the medium the wafer shall be exposed to. The medium will be supplied via a channel 2111 in the panel 21 to the needle head 1. The panel 21 of FIG. 2 comprises a slab 211 and an enclosure 212 for the slab 211. The channel 2111 is formed between the slab 211 and the enclosure 212. An opening 214 of the panel 21 is provided for holding the needle head 1. The channel 2111 ends at an outlet 2121 in the opening 214. A channel 15 in the needle head 1 provides inlets 14 at sidewalls 1131 of the frame 113 of the needle head 1 wherein these inlets 14 are aligned with the outlets 2121 of the channel 2111 such that a medium supplied by the channel 2111 of the panel 21 will enter the channel 15 of the needle head 1. When entering the channel 15 of the needle head 1, the medium will propagate through an aperture 11431 of the top layer 1143 of the needle holder 114 into the chamber 1144, and will leave the needle head 1 out of the outlets (not shown) in the lower surface 111 of the needle head 1, i.e. the lower surface 111 of the bottom layer 1143.

Figure 5:
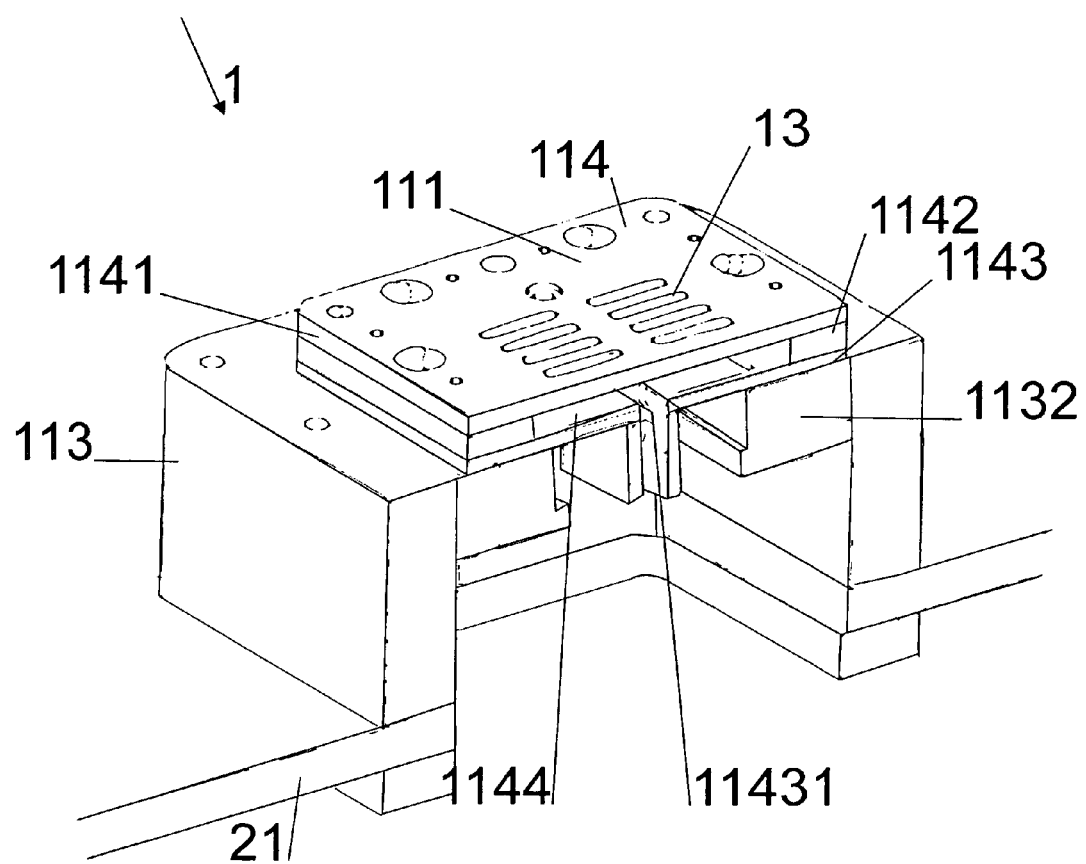

For a better understanding of the medium flow between the interior of the frame 113 and the outlets of the needle head 1, it is referred to FIG. 5. FIG. 5 shows a similar needle head 1 in a cut open view. In this perspective, the needle holder 114 with its three layers 1141, 1142 and 1143 is mounted to a mounting platform 1132 of frame 113. The three layers 1141, 1142 and 1143 define the chamber 1144. Especially, it becomes apparent that the aperture 11431 in top layer 1143 builds an interface for the medium between the frame 113 and the needle head 114. FIG. 5 also illustrates the outlets 13 in the bottom layer 1141 for the medium to exit the needle head 1. In this embodiment, the needle head 1 is mounted to a panel 21.

In the embodiment of FIG. 2, the frame 113 of the needle head 1 comprises a central opening at its top. Such opening advantageously is closed by a plug in order not to allow the medium to exit the frame 113 at this location but instead make the medium completely exit the needle head 1 through the needle holder 114. However, in an alternative embodiment, the inlets 14 in sidewalls 1131 of the frame 113 may be closed, e.g. by plugs, or not even be provided in these sidewalls 1131, such that the central opening may serve as inlet 14 for the medium. In such case, the medium may be supplied from the top of the needle head 1. However, the channel 2111 in the panel 21 may still serve for forwarding the medium to outlets in the panel 21 (not shown).

Figure 3:
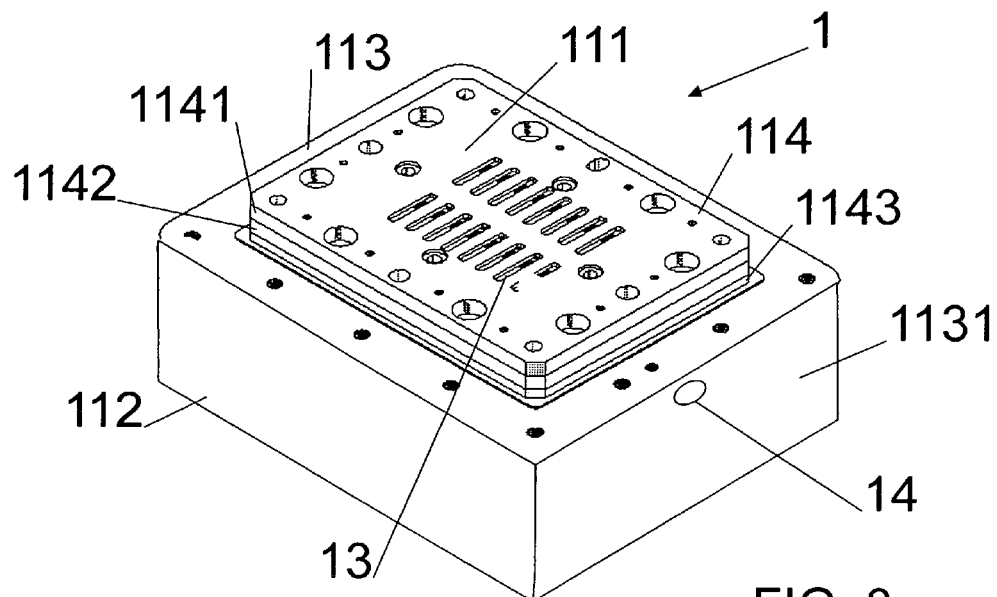

FIG. 3 illustrates a perspective view of a needle head 1 according to an embodiment of the invention which needle head 1 is similar to the one introduced in FIG. 2. Again, the needle head 1 is basically of rectangular shape and comprises a frame 113 and a needle holder 114, the needle holder 114 in turn comprising three layers 1141, 1142 and 1143. As can be seen from FIG. 3, the frame comprises two inlets 14 in form of bores—of which only one bore is visible in its sidewalls 1131—for allowing a medium to enter the inner channel structure of the needle head 1.

The bottom layer 1141 basically has a plain lower surface 111 which is interspersed with holes serving for different purposes. The holes at the outer perimeter of bottom layer 1141 serve for mounting the layers of the needle holder 114 to the frame 113. The elongated holes arranged in parallel to each other in two rows serve as outlets 13 for the medium supplied to the needle head 1. Additionally, there are bores (not shown) for the needle electrodes to pass through the bottom layer 1141 and emerge from the lower surface 111 of the needle head 1. Advantageously, each needle electrode is arranged in a separate needle bore in said lower surface 111. In a preferred embodiment, a combined area of needle bores and outlets covers an area less than a third of the lower surface 11.

Figure 4:
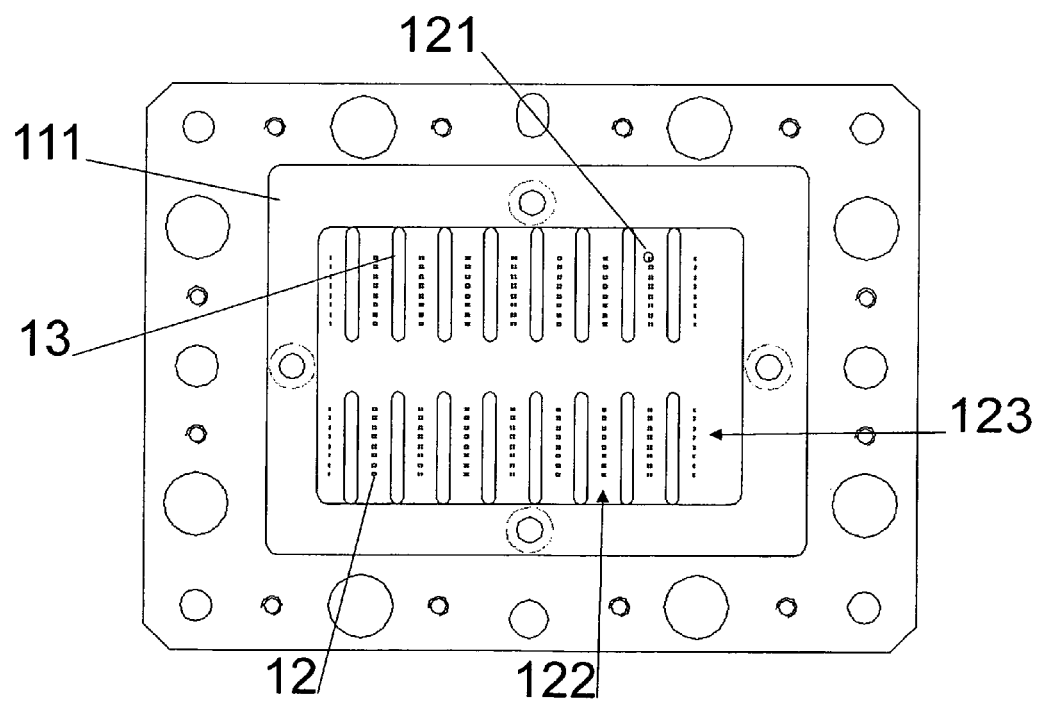

In FIG. 4, which is a plan view on the lower surface 111 of the needle head 1 according to FIG. 3, the bores for the needle electrodes 12 are indicated by a small dot. In this embodiment, a separate bore in the bottom layer 1141 is assigned to each needle electrode 12. Such arrangement serves best for isolating the needle electrodes 12 when being compressed in z-direction. However, there may be embodiments where a common bore may serve for two or more needle electrodes, and in particular for all needle electrodes contacting the same electronic component.

In FIG. 4, a pair of two needle electrodes forms a subgroup 121 of needle electrodes 12, which subgroup 121 is arranged to contact one sensor on the wafer 8. The electrodes 12 of the same subgroup 121 are arranged close to each other, and in particular closer to each other than to any other needle electrode 12 of the needle head 1. The needle electrodes 12 of a subgroup 121 are arranged such that contact pads of the electronic component provided in the wafer can properly be contacted. Eight of these subgroups 121 are arranged close to each other in from of a column. The subgroups 121 of the same column form a group 122. The subgroups 121 belonging to the same group 122 do have a distance to the neighbouring subgroup 121 smaller than to any other subgroup 121 of the needle head 1. The groups 122 of needle electrodes 12 are arranged in two rows 123 in the present example. In each row 123, the neighbouring groups 122 are separated from each other by an elongated outlet 13. By means of such arrangement, it is achieved that the area where the sensors are contacted by the needle electrodes 12 for calibrating or testing purposes are sufficiently exposed to the medium during such testing operation. The outlets 13 are arranged very close to the needle electrodes 12. At the same time, the needle electrodes 12 may be fixed in the top layer 1143 by that allowing the needle electrodes 12 to take a straight shape. An excessive lateral movement of the needle electrodes 12 potentially causing damage is prevented by the bores in which the needle electrodes 12 are guided laterally.

For calibrating sensors with a needle head according to one of the previous Figures, a wafer 8 comprising a plurality of sensors to be calibrated is placed on chuck 7, either manually or automatically. A humidity generator is activated to generate a gas with a known humidity level. The humid gas is fed through a tube to the channel 2111 structure in the panel 21. During its passage through the channel 2111, the gas will be thermalized to a given temperature by the heating/cooling means such that when arriving at the needle head 1, the gas substantially shows the given temperature and therefore a defined relative humidity.

The gas will pour into the channel 15 or the needle head 1 and emanate from the outlets 13 in the lower surface 111 of the needle head 1 such that the sensors to be calibrated are directly exposed to such gas. By such means, a defined environment is granted during calibration resulting in more accurate calibration results. Additionally, the gas may emanate from the panel itself 21 through outlets 2121 arranged in the lower surface of the panel 21. The channel structure for feeding these outlets 2121 may include the same channel 2111 for supplying the needle head 1 with gas. Alternatively, a separate channel in the panel may be used for conveying the gas to the outlets 2121 in the panel 21.

While the wafer 8 is exposed to the calibration gas, the sensors on the wafer 8 can preferably all be calibrated simultaneously provided the needle head 1 provides sufficient needle electrodes 12 for contacting all the sensors at the same time. Alternatively, the sensors are contacted sequentially by displacing the chuck 7 and the panel 21 relative to each other in x/y direction. The calibration itself may comprise a calibration measurement and subsequent storage of calibration data in the sensor itself. Advantageously the calibration data is stored in the sensor immediately after calibrating it.

During calibration, the general functionality of each sensor can be tested as well, and malfunctioning sensors can be discarded after cutting the wafer 8. Once the calibration of the sensors on wafer 8 is complete, the wafer 8 can be removed from the wafer prober, either manually or automatically, and be cut for separating the individual sensors.

In the above examples, the invention has been explained in the context of an advantageous application, namely the calibration of humidity sensors. As explained above, however, the invention can also be used for calibrating other types of sensors detecting a substance in a fluid. In particular, it can be used for sensors detecting substances in gases or the composition of a gas mixture, in which case the humidity generator is replaced by a suitable device for preparing a mixture of gases with a defined ratio. Typical substances are $CO$, $CO_2$, $NO_x$, volatile organic compounds (VOC), any type of gaseous organic compounds, and any other types of compound.

The invention could even be used for sensors adapted to measure a substance in a liquid, as long as the liquid allows the operation of the needle head 1. In that case, the wafer prober may be arranged in a bath of the liquid. Advantageously, when being used for calibrating sensors detecting a substance in a fluid, the apparatus may be provided with a suitable fluid feed for feeding the calibration fluid to the channel structure in the needle head and the panel respectively.

The types of apparatus described here can also be used for calibrating temperature sensors on the wafer. In particular, having a temperature controlled panel and a temperature controlled chuck allows generating a highly homogeneous temperature distribution in the wafer, in particular if the panel and the chuck are kept at the same temperature. To calibrate temperature sensors on a wafer, the wafer is placed on the chuck and exposed to such temperature. Calibration measurements can be carried out by means of the needle head.

If the apparatus is used for temperature sensor calibration, it is not necessary to provide a fluid feed as it is used for the calibration of substance sensors.

The invention claimed is:

1. A needle head for electrically contacting an electronic component, comprising
   a body with a lower surface,
   needle electrodes emerging from said lower surface,
   multiple outlets arranged in said lower surface, and
   a channel between an inlet in said body and said outlets for conveying a medium from said inlet to said outlets.

2. A needle head according to claim 1, wherein said needle electrodes are arranged in needle bores in said lower surface, said needle bores forming openings in said lower surface separate form said outlets.

3. A needle head according to claim 2, wherein each needle electrode is arranged in a separate needle bore in said lower surface, and wherein a combined area of needle bores and outlets covers an area less than a third of said lower surface.

4. A needle head according to claim 1, wherein said needle electrodes are arranged in subgroups with each subgroup being designed for contacting an individual electronic component, said subgroups being arranged in groups, said groups being arranged in at least one row, and one of said outlets being arranged between each two neighbouring groups of the same row.

5. A needle head according to claim 1, wherein each outlet is formed by an elongated hole.

6. A needle head according to claim 1, wherein said inlet is arranged in a side surface of said body.

7. A needle head according to claim 1, wherein said body comprises a frame made out of metal and forming at least sidewalls of said body, and wherein said at least one inlet is arranged in said side walls.

8. A needle head according to claim 2, wherein said body comprises a layered needle holder with a bottom layer including said outlets and said needle bores, with said bottom layer forming said lower surface of said body, and with a top layer for holding said needle electrodes said top layer including an aperture forming part of said channel.

9. A needle head according to claim 8, wherein an intermediate layer in form of a frame is arranged between said bottom layer and said top layer for forming a chamber together with the top and the bottom layer, and wherein said layers are made out of ceramics.

10. A probe arrangement, comprising
a panel with a lower surface,
a channel in said panel for conveying a medium,
at least one outlet arranged in said lower surface of said panel and connected to said channel, and
a needle head according to claim 1 arranged in an opening of said panel.

11. A probe arrangement according to claim 10, wherein said channel of said panel is connected to said channel of said needle head.

12. A probe arrangement according to claim 10, comprising an outlet in said opening of said panel, and an inlet arranged in a side surface of said body of said needle head, wherein said outlet in said opening and said inlet at said side surface are aligned.

13. A probe arrangement according to claim 10, comprising means for heating or cooling the panel.

14. A probe arrangement according to claim 10, comprising means for heating or cooling the needle head.

15. A probe arrangement, comprising
a panel with a lower surface,
a channel in said panel for conveying a medium,
a needle head according to claim 1 arranged in an opening of said panel,
wherein said channel of said panel is connected to said channel of said needle head.

16. A probe arrangement according to claim 15, comprising at least one outlet arranged in said lower surface of said panel and connected with said channel of said panel.

17. A probe arrangement according to claim 15, comprising an outlet in said opening of said panel, and an inlet arranged in a side surface of said body of said needle head, wherein said outlet in said, opening and said inlet at said side surface are aligned.

18. A probe arrangement according to claim 15, comprising means for heating or cooling the panel.

19. A probe arrangement according to claim 15, comprising means for heating or cooling the needle head.

20. A method for electrically contacting multiple electronic components, comprising
providing a wafer including said electronic components,
providing a needle head according to claim 1,
supplying said inlet of said needle head with said medium,
bringing said electronic components simultaneously into contact with said needle electrodes,
measuring signals accessible at said needle electrodes.

* * * * *